May 8, 1973 B. J. MACHIN Plant Pat. 3,326
CHRYSANTHEMUM PLANT
Filed May 18, 1971
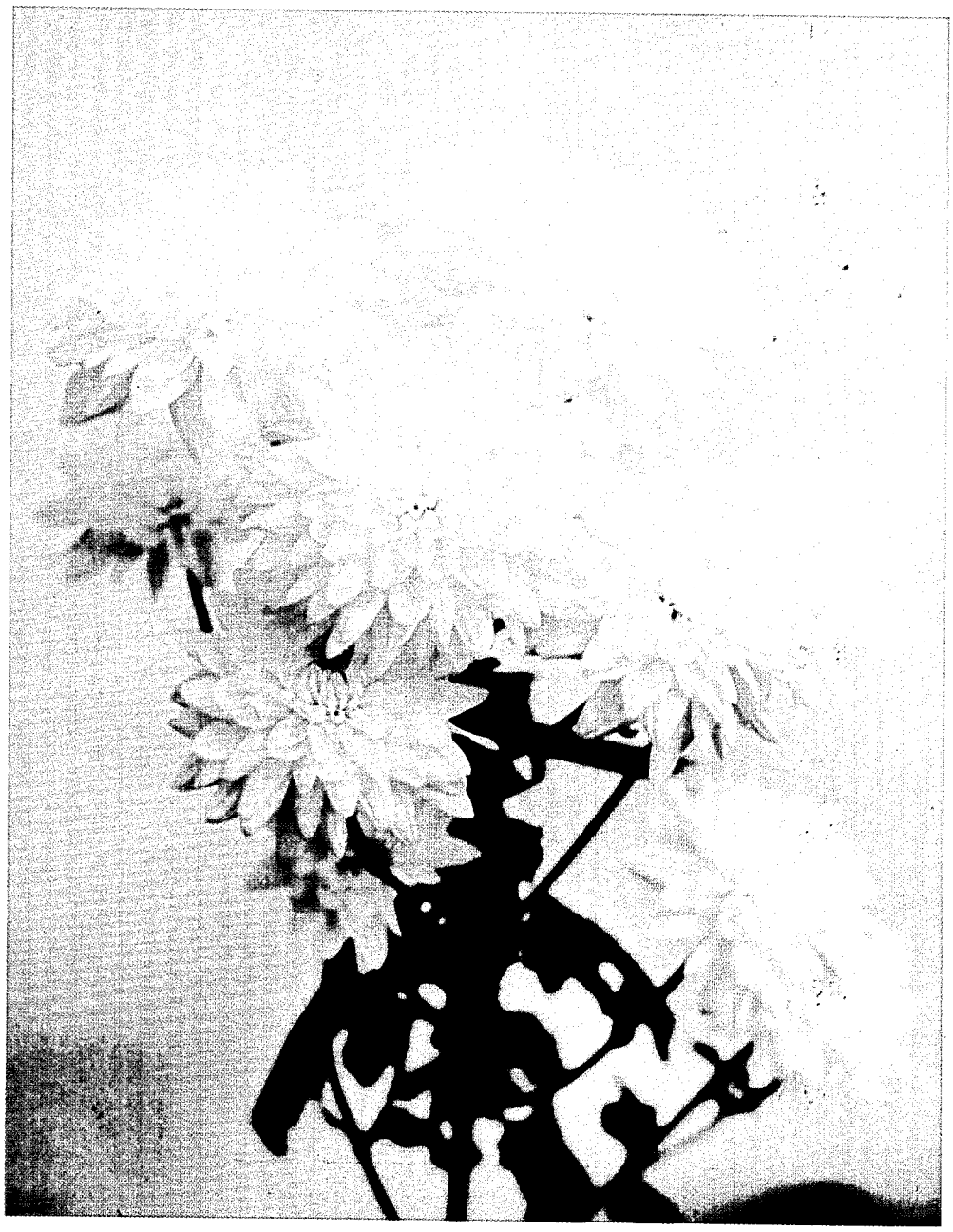

United States Patent Office

Plant Pat. 3,326
Patented May 8, 1973

3,326

CHRYSANTHEMUM PLANT

Barrie John Machin, Chichester, England, assignor to Framptons Nurseries Limited, Worthing, Sussex, England

Filed May 18, 1971, Ser. No. 144,695
Int. Cl. A01h *5/00*
U.S. Cl. Plt.—77 1 Claim

This invention relates to a new and distinct variety of *Chrysanthemum morifolium* Bailey (spray type), hereinafter referred to as "Arctic."

My new variety was originated by me by crossing the known *Chrysanthemum morifolium* Bailey variety "Saturn" with a seedling of unknown parentage which was produced in the course of a previous cross-breeding program, with "Saturn" being the seed parent and the unknown seedling the pollen parent.

This new variety resulted from an extensive breeding program with the objective of producing an open terminal spray type dependable under a wide variety of controlled year-round (greenhouse) and/or natural season growing conditions.

Arctic has the color of Iceberg, the strength and vigor of Hurricane, and the fast response of Polaris, with better uniformity over a wide variety of growing conditions.

The following unique combination of characteristics distinguish Arctic from its parents, as well as from all other Chrysanthemum varieties of which I am aware:

(1) A vigorous plant of strong, upright habit, producing 44 inch stems on a single stem crop with five long day weeks.

(2) Flower borne on pedicels, with 8–16 flowers per main stem as a spray type.

(3) Double petals with 200–250 thick, broad, overlapping blunt and slightly curled ray petals, with 5–10 disc petals.

(4) Response time of 9 weeks.

(5) Dependable under wide range of growing conditions, tolerating night temperatures of 55–60° F. without loss of ability to initiate and develop flowers, or pinking of florets.

(6) Color approximating that of Iceberg, ranging from RHS 155B to RHS 158D.

As compared with existing white spray types, as a group, Arctic has the color of Iceberg, the strength and vigor of Hurricane, and the fast response of Polaris, with better uniformity over a wide variety of growing conditions. As compared with specific types, Arctic has the following advantages over representative most nearly similar varieties:

(1) As compared with Hurricane has:

(a) No clubby sprays (i.e. with very short pedicels) in spring crops.
(b) More vigor requiring no extra long day growing time.
(c) Better breaking action for pinched crops.
(d) No problems due to abortion of the growing point.
(e) More flowers per spray.

(2) As compared with Iceberg, Arctic has:

(a) No pinking of the florets when finished in cool temperatures.
(b) No known foliar or stem rot problems.
(c) The ability to initiate and develop flowers in 56° F. minimum night temperatures.
(d) More flowers per spray resulting in higher market grades.

(3) As compared with No. 2 Whitechip, Arctic has (a) No pinking of the florets when finished in cool temperatures.

(b) Better breaking action for pinched crops.
(c) More flowers per spray resulting in higher market grades.

As compared with its seed parent, Arctic has a larger flower, more flowers per stem and a shorter, stronger habit of growth. Color is ivory white rather than yellow.

As compared with its pollen parent, Arctic has a wider branching spray type and longer and stronger pedicels.

Asexual reproduction of this new variety as performed in Sussex, England, by rooting vegetative shoots, shows that the above characteristics are fixed and come true to type and are transmitted through succeeding generations.

The accompanying drawing shows a typical flower of my new variety depicted in color as nearly true as it is reasonably possible to make the same in a color illustration of this character.

The following is a detailed description of the new variety Arctic, with color terminology in accordance with the Royal Horticultural Society Colour Chart (RHS) and the Horticultural Colour Chart (HCC).

Genus—Chrysanthemum.
Species—*Morifolium* Bailey.
Type—Spray.
Class—Decorative.
Breeding—Seedling—Seed parent BGA Saturn Pollen parent, unknown seedling.

*Propagation.*—Holds its distinguishing characteristics through succeeding propagations by rooting vegetative shoots.

*Locality where grown and observed.*—Sussex, England.

*Flower.*—Borne on pedicels 8 to 16 flowers per main stem as a spray type.

*Bloom.*—Size 2–2½ inches in diameter when fully open. Petalage—Double 200–250 ray petals. 5–10 disc petals. Form—Decorative and rather flat. Petals—Thick and broad, overlapping, blunt and slightly curled. Color of open bloom—Inner face of fully expanded petal RHS 155B. Outer face of fully expanded petal RHS 155D. Inner face of young petal RHS 158B (Chrome Yellow HCC 6053). Outer face of young petal RHS 158D.

*Response group (weeks of short days to flower).*—9 weeks.

*Temperature tolerance.*—55–60° F. at night.

*Plant.*—Strong upright habit. Produces 44 inch thick strong stems on a single stem crop with five long day weeks. Water uptake good. Color of stems at flowering RHS 138C. Pedicels thick and fairly long (4–8 inches), flowers held at an angle of about 60° to the main stem.

*Foliage.*—Medium quantity. Average internode length 1 inch. Medium size and texture. Color of young leaves RHS 138A, mature leaves RHS 138B.

I claim:

1. A new and distinct variety of *Chrysanthemum morifolium* Bailey, substantially as herein shown and described, characterized particularly as to novelty by the unique combination of a vigorous plant of strong, upright habit, with 8–16 pale flowers per main stem, said flowers having an average of 200–250 double petals, said plant having a response time of nine weeks and tolerating a night temperature of 55–60° F. without loss of ability to initiate and develop flowers or pinking of florets.

No references cited.

ROBERT E. BAGWILL, Primary Examiner